United States Patent
Bartl

(10) Patent No.: US 9,662,082 B2
(45) Date of Patent: May 30, 2017

(54) METHOD AND APPARATUS FOR ELECTRONIC CORRECTION OF DIGITAL PROJECTION DATA

(71) Applicant: SIEMENS AKTIENGESELLSCHAFT, Munich (DE)

(72) Inventor: Peter Bartl, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 64 days.

(21) Appl. No.: 14/825,348

(22) Filed: Aug. 13, 2015

(65) Prior Publication Data

US 2016/0045179 A1 Feb. 18, 2016

(30) Foreign Application Priority Data

Aug. 13, 2014 (DE) .......................... 10 2014 216 073

(51) Int. Cl.
*A61B 6/00* (2006.01)
*A61B 6/02* (2006.01)
*G06T 11/00* (2006.01)

(52) U.S. Cl.
CPC ............ *A61B 6/5223* (2013.01); *A61B 6/025* (2013.01); *A61B 6/502* (2013.01); *A61B 6/5205* (2013.01); *G06T 11/005* (2013.01); *G06T 2200/04* (2013.01); *G06T 2207/10116* (2013.01); *G06T 2211/436* (2013.01)

(58) Field of Classification Search
CPC ....... G06T 5/007; G06T 5/009; G06T 7/0018; G06T 7/002; G06T 11/005; G06T 2207/10112; A61B 6/025; A61B 6/52; A61B 6/5211; A61B 6/5223; A61B 6/5258; A61B 6/582; A61B 6/585
See application file for complete search history.

(56) References Cited

U.S. PATENT DOCUMENTS

| | | | |
|---|---|---|---|
| 2004/0120468 A1* | 6/2004 | Dhawale et al. ............. | 378/207 |
| 2005/0117708 A1 | 6/2005 | Cho et al. ...................... | 378/164 |
| 2006/0120506 A1* | 6/2006 | Li et al. ......................... | 378/21 |
| 2010/0054400 A1 | 3/2010 | Ren et al. ...................... | 378/37 |

(Continued)

FOREIGN PATENT DOCUMENTS

JP 2008220726 A 9/2008

OTHER PUBLICATIONS

Sidky E. Y. et al; "Enhanced imaging of micro calcifications in digital breast tomosynthesis through improved image-reconstruction algorithms"; Med. Phys vol. 36, No. 11; pp. 4920-4932; 2009.

*Primary Examiner* — Andrew W Johns
(74) *Attorney, Agent, or Firm* — Laurence Greenberg; Werner Stemer; Ralph Locher

(57) ABSTRACT

A method and an apparatus for creating a correction map for electronic correction of digital projection data from which it is possible to reconstruct a tomosynthetic 3D X-ray image. Furthermore, a method and apparatus are described for electronic correction of digital projection data. In order to allow particularly simple correction of digital projection data, the creation of the correction map includes a reconstruction of the lowermost layer of the 3D X-ray image to be reconstructed from the digital projection data, which lowermost layer corresponds to the detector plane of the digital X-ray detector.

9 Claims, 1 Drawing Sheet

(56) References Cited

U.S. PATENT DOCUMENTS

2011/0057802 A1\* 3/2011 Topfer et al. .................. 340/584
2012/0087481 A1   4/2012 Litvin et al. .................. 378/207
2014/0050301 A1\* 2/2014 Liu ................................ 378/62

\* cited by examiner

METHOD AND APPARATUS FOR ELECTRONIC CORRECTION OF DIGITAL PROJECTION DATA

CROSS-REFERENCE TO RELATED APPLICATION

This application claims the priority, under 35 U.S.C. §119, of German patent application DE 10 2014 216 073.1, filed Aug. 13, 2014; the prior application is herewith incorporated by reference in its entirety.

BACKGROUND OF THE INVENTION

Field of the Invention

The invention relates to a method and an apparatus for creating a correction map for the electronic correction of digital projection data, recorded with a digital X-ray detector, from which projection data it is possible to reconstruct a tomosynthetic 3D X-ray image. Furthermore, the invention relates to a method and an apparatus for the electronic correction of digital projection data.

Tomosynthetic image reconstruction methods are known that involve a tomosynthetic 3D X-ray image being compiled from a plurality of digital frames recorded at different projection angles in a limited angle range or from projection data that are respectively associated with these frames. Such image reconstruction data are particularly suitable for mammography, that is to say, for X-ray examination of the female breast, with the aim of identifying tumors at the earliest possible stage.

This involves the digital frames or projections recorded from different projection directions, i.e. the image data associated with these frames, being used to produce an image data record that consists of a plurality of layer images, for example, that each reproduce a layer of the object to be examined, for example the breast, that is oriented parallel to the reception area of the X-ray detector. Such an image data record is referred to as a tomosynthetic 3D X-ray image in this case.

The image data record is produced from the projection data using a suitable image reconstruction method, for example by means of filtered back-projection, a method that involves the measurement data provided by the X-ray detector, the projection data, being back-projected on to a volume matrix, namely the digital 3D image of the object, after these measurement data have previously been subjected to suitable filtering, in order to identify clinically relevant structures of the object.

In digital X-ray imaging, the X-ray detectors used are frequently flat panel detectors having an active reading matrix with direct or indirect conversion of the X-ray radiation. In this case, the entire area of the active matrix (detector area or reception area) is divided into a multiplicity of pixel reading units. The X-ray radiation converted into electrical charge in the reading matrix is stored in the matrix in spatially resolved fashion and can be read using electronics that use suitable analog-to-digital converters to produce corresponding image data.

In order to improve image quality, it is customary to calibrate these X-ray detectors. The aim of calibration is to electronically correct some effects caused by the specific properties of the respective X-ray detector.

In order to balance out sensitivity fluctuations in the X-ray detector and in order to compensate for the basic contrast, gain correction is usually effected, which involves an objectless calibration image being recorded at a constant X-ray illumination. This gain calibration image recorded beforehand or even following the actual measurement is linked to the X-ray images recorded during clinical operation of the X-ray detector, so that the basic contrast that is present in both images is at least to some extent removed. In the case of what is known as offset correction, the brightness is compensated for in a similar manner. However, this involves the production of an offset calibration image that is recorded in the absence of X-ray radiation. In general, offset corrections are made by means of electronic subtraction and gain corrections are made by means of electronic multiplication of the projection data with the created offset or gain calibration images.

The calibration images are thereby created independently of clinical measurements, i.e. without an object to be examined in the beam path. Image reconstructions do not take place in this case. Nevertheless, such a calibration operation is comparatively complex and is therefore normally effected only at relatively long intervals of time. This can result in the image quality of the X-ray radiographs changing in the course of operation of the X-ray apparatus. This can negatively influence the medical significance of the X-ray images obtained.

Furthermore, the prior creation of calibration images frequently becomes very much more complex when measurement and/or environmental parameters, that later change, need to be taken into account already. An example of this is the temperature of the X-ray detector. Temperature changes in the X-ray detector are known to result in offset structures and sensitivity differences primarily at border regions and transition regions of the active matrix or of the X-ray converter. In order to prevent the occurrence of miscorrections when the measurement data are recorded by the X-ray detector at different temperatures than the calibration images in the course of operation, calibration images are therefore often created for different temperatures in advance already. A plurality of calibration images are normally also created for different X-ray doses. From the multiplicity of calibration images created in advance and kept ready later, it is then also necessary for the correct calibration image to be selected and applied during the clinical recordings.

SUMMARY OF THE INVENTION

It is accordingly an object of the invention to provide a method and apparatus for the correction of digital projection images which overcome the above-mentioned and other disadvantages of the heretofore-known devices and methods of this general type and which provide for a particularly simple correction of digital projection data.

With the foregoing and other objects in view there is provided, in accordance with the invention, an X-ray method, comprising:

recording digital projection data with a digital X-ray detector having a detector plane, the projection data being suitable for reconstruction of a tomosynthetic 3D X-ray image having layers;

creating a correction map for an electronic correction of the digital projection data recorded by the digital X-ray detector, the step of creating the correction map including a reconstruction of a lowermost layer of the 3D X-ray image from the digital projection data, the lowermost layer corresponding to the detector plane of the digital X-ray detector.

With the above and other objects in view there is also provided, in accordance with the invention, an apparatus for creating a correction map for electronic correction of digital projection data, the apparatus comprising:

an input for receiving digital projection data recorded by a digital X-ray detector, wherein the projection data are suitable for a reconstruction of a tomosynthetic 3D X-ray image; and wherein the apparatus is configured to reconstruct a lowermost layer of the 3D X-ray image from the digital projection data, wherein the lowermost layer corresponds to a detector plane of the digital X-ray detector.

Furthermore, there is provided a method for electronic correction of digital projection data recorded by a digital X-ray detector, wherein the digital projection data are suitable for a reconstruction of a tomosynthetic 3D X-ray image. The novel method comprises correcting the projection data with a correction map created by the herein-described method.

There is also provided, in accordance with the invention, an apparatus for electronic correction of digital projection data, wherein the projection data are recorded with a digital X-ray detector, and the projection data are suitable for reconstructing a tomosynthetic 3D X-ray image. The novel apparatus is configured to correct the projection data using a correction map created on the basis of there herein-described novel method.

In other words, the method according to the invention for creating a correction map for electronic correction of digital projection data, recorded using a digital X-ray detector, from which projection data it is possible to reconstruct a tomosynthetic 3D X-ray image is distinguished in that the creation of the correction map involves the reconstruction of the lowermost (i.e., bottommost) layer of the 3D X-ray image to be able to be reconstructed from the digital projection data, which layer corresponds to the detector plane of the digital X-ray detector.

The method according to the invention for electronic correction of these digital projection data is distinguished in that the projection data are corrected using a correction map that has been created on the basis of the method specified above.

The apparatuses according to the invention are designed to perform the methods according to the invention.

The advantages and refinements that are explained below in connection with the method also apply mutatis mutandis to the apparatus according to the invention, and vice versa.

A central concept of the invention is for the previously pursued approach of calibrating a digital X-ray detector using previously recorded calibration images no longer to be pursued further. There is therefore also no longer any need to perform such a calibration method in a manner that is as timesaving as possible by applying a wide variety of optimization measures.

Instead, the invention provides a technology that can be used to completely dispense with complex and time-consuming, and, for all that, never optimum, calibration of the X-ray detector using calibration images, recorded for this purpose, in the case of tomosynthetic imaging methods from the outset.

The separately created calibration images are replaced by a correction map that is created from the tomosynthetic measurement in a manner exact to the recording. According to the invention, the tomosynthetic imaging method does not just involve the use of a reconstruction method, such as the use of filtered back-projection, to create the actual 3D X-ray image. Furthermore, the creation of the correction map also involves the reconstruction of the lowermost layer of the 3D X-ray image to be able to be reconstructed from the digital projection data, which layer corresponds to the detector plane of the digital X-ray detector. In other words, the invention proposes the use of an image reconstructed from the projection data, i.e. an image reconstructed from the measured values of the X-ray radiograph, for correction purposes.

The correction map according to the invention is produced from the data of the tomosynthetic measurement. Additional calibration measurements are dispensed with. This involves the lowermost layer to be able to be reconstructed from the projection data, i.e. the measurement data from the X-ray detector, being ascertained using a suitable reconstruction method. This lowermost reconstructed layer is used to depict the detector plane. In other words, this layer in the tomosynthetic 3D X-ray image corresponds to the reception area of the X-ray detector, that is to say precisely that area at which the X-ray radiation is converted into electrical charge. This means that this lowermost layer reflects all the specific properties of the X-ray detector, to be more precise the properties of the multiplicity of single detectors in the digital X-ray detector. This lowermost layer does not contain any information that changes during the individual recordings at different projection angles about the object to be examined, but instead comprises everything immobile and hence all the information associated with the X-ray detector.

Preferably, this lowermost layer is reconstructed by means of an unfiltered reconstruction method, for example by means of unfiltered back-projection. This lowermost layer, to be more precise the image of this lowermost layer, the image points of which correspond to the detector pixels of the X-ray detector, can therefore be used as a recording-exact correction map for electronic correction, or this image can be used to create a recording-exact correction map for electronic correction. Preferably, the correction map is a gain correction map for performing electronic gain correction.

In a simple exemplary embodiment of the invention, reconstruction of the lowermost object layer is simply followed by further reconstruction. In other words, it may be that a plurality of "empty layers" are reconstructed, even though there is no longer an object at that location. Prior to the reconstruction of the lowermost layer associated with the X-ray detector, a possibly still active filter is switched off, so that the then reconstructed layer depicts the properties of the X-ray detector in a pixel-exact fashion.

Advantageously, the reconstructed detector plane can be used as correction map or for creating a correction map even when there is an object in the beam path, since the object structures in this plane are no longer visible. In other words, the layer reconstructed for the purpose of creating the correction map may be the lowermost layer of a 3D X-ray image of an object to be examined that is recorded during a clinical tomosynthetic recording. In other words, a real medical recording can be used in order to create the desired correction map therefrom. It is merely necessary to perform a further reconstruction, namely the reconstruction of the lowermost layer.

In this case, the correction map is always based on the same recording parameters as the clinical X-ray radiograph. This means that the correction map is always up to date and recording-exact and contains all the pieces of information concerning the X-ray detector that are associated with the respective X-ray radiograph or measurement. It is therefore firstly no longer necessary to keep a multiplicity of calibration images etc. for all possible parameters, such as temperature and dose, and to select the correct calibration image. Secondly, it is also possible to store and/or evaluate recording-exact correction maps or to evaluate correction maps and to store the evaluation results. Furthermore, it is possible to compare the stored data to one another in order to draw conclusions therefrom about the operating behavior of the X-ray detector, for example in order to identify the effects of aging on the X-ray detector. Finally, it is therefore likewise possible to monitor the detector properties and the changes therein over time.

Iterative application of the correction maps obtained in this manner is particularly advantageous. Preferably, the creation of a respective further correction map involves the fresh reconstruction of the lowermost layer of the 3D X-ray image to be able to be reconstructed from the respective already corrected digital projection data, which layer corresponds to the detector plane of the digital X-ray detector. This achieves a qualitative improvement in the correction. Normally, the result converges after a few iteration steps.

The present invention allows not just particularly simple correction, particularly gain correction, of digital projection data. The proposed method is also time-saving and reliably prevents the application of an incorrect or inexact correction. Calibration of the X-ray detector in the conventional sense is no longer necessary.

Other features which are considered as characteristic for the invention are set forth in the appended claims.

Although the invention is illustrated and described herein as embodied in the electronic correction of digital projection data, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
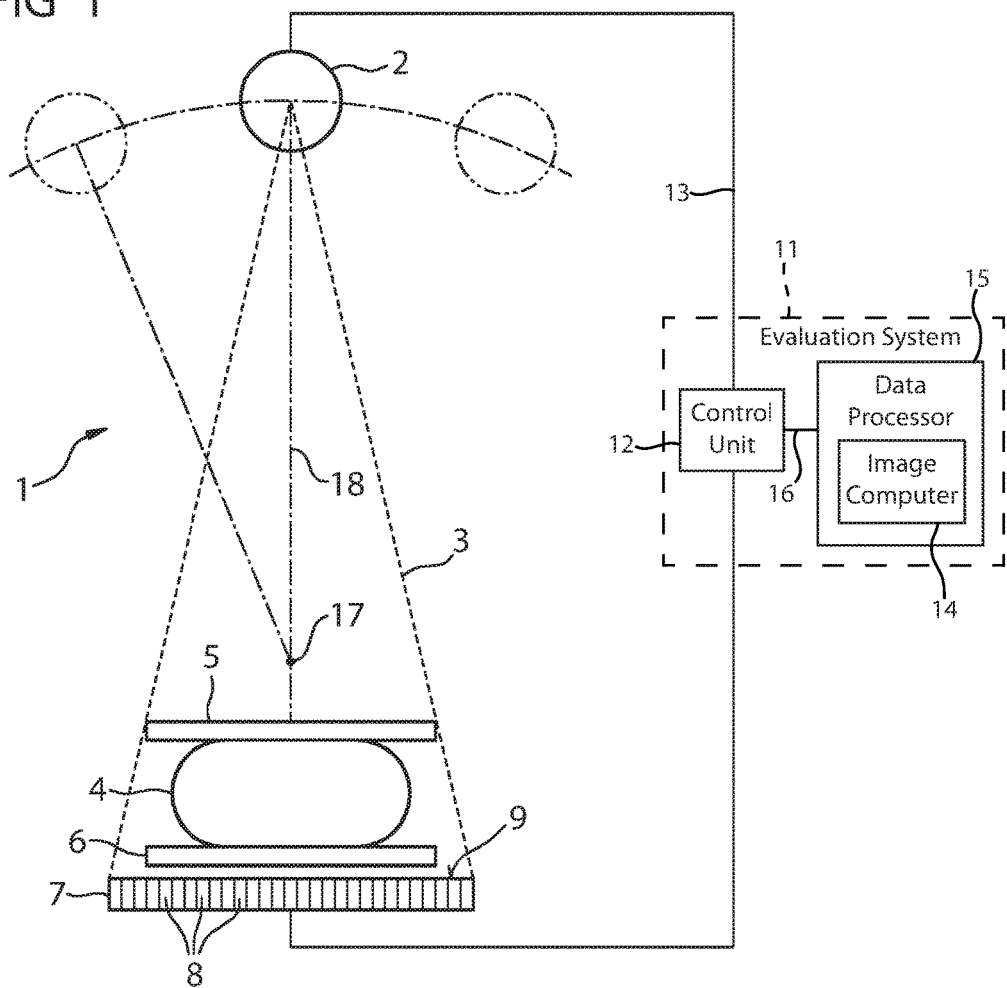
FIG. 1 shows a schematic X-ray apparatus according to the invention.
Figure 2:
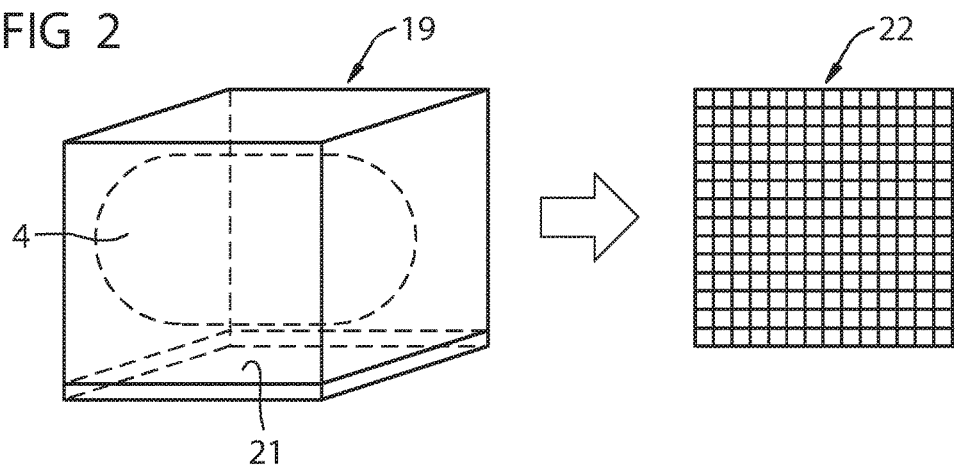
FIG. 2 shows a schematic illustration of the lowermost layer and the correction map.

Referring now to the figures of the drawing in detail and first, particularly, to FIG. 1 thereof, there is shown an X-ray apparatus 1 embodied as a mammography appliance. The X-ray apparatus 1 comprises an X-ray source 2 in the form of an X-ray tube for producing X-rays 3 that pass through an examination object 4. The examination object 4 is a female breast that is embedded between a compression plate 5 and a support plate 6. The X-rays 3 passing through the examination object 4, the compression plate 5 and the support plate 6 are received by a large-area digital X-ray detector 7 that is arranged in the path of radiation. The detector 7 is constructed from a multiplicity of single detectors 8 arranged in a matrix array, and the reception area 9 of which is arranged parallel to the plates 5, 6.

The X-ray apparatus 1 additionally comprises a control and evaluation system 11. The control and evaluation system 11 comprises a control unit 12 for actuating the X-ray source 2 and/or the X-ray detector 7 and also for producing a supply voltage for the X-ray source 2. The control unit 12 is connected to the X-ray source 2 via data and supply lines 13. The control and evaluation system 11 additionally comprises an image computer 14 that is designed for image handling and image processing and is preferably a software component of a data processing installation 15. The data processing installation 15 additionally contains a piece of user software for the X-ray apparatus 1. The data processing installation 15 is connected to the control unit 10 and the X-ray detector 7 via data and system bus lines 16. It is additionally connected to peripheral devices, particularly a screen, a keyboard and a mouse, for the purpose of inputting and outputting data.

In order to perform the tomosynthetic recordings, the X-ray tube 2 is arranged in a delimited region in relation to the examination object in a manner such that its location can be altered, and can be swiveled into different angle positions, for example in a delimited angle range about an axis 17 perpendicular to the plane of the drawing, so that frames can be produced from the examination object 4 at different projection angles relative to the normal 18 to the reception area 9 of the fixed X-ray detector 7.

The manner of operation of a suitable X-ray detector 7 is known to a person skilled in the art and therefore does not need to be specified in detail at this juncture. The charge stored in the X-ray detector 7 can then be read by means of detector-inherent electronics (not shown), with digital image data being produced by way of amplification and analog-to-digital conversion of the charge that is read. The image data are transmitted to the image computer 14 via the data and system bus line 16.

According to the invention, gain correction for the image data or the corresponding projection data is then effected by means of the image computer 14. To this end, the image computer 14 creates a gain correction map 22 by reconstructing the lowermost (=bottommost) layer 21 of the 3D X-ray image 19, recorded during the tomosynthetic recording, to be able to be reconstructed from the projection data, which layer corresponds to the detector plane 9 of the X-ray detector 7, by means of an unfiltered reconstruction method, for example by means of unfiltered back-projection. The image of this lowermost layer 21, which image reproduces the properties of the X-ray detector 7, is then used by the image computer 14 as a gain correction map 22 for electronic gain correction for the digital projection data.

For the purpose of gain correction, a first gain correction map is first of all created in the image computer 14. Next, the projection data are corrected in the image computer 14 using the first gain correction map by linking them through multiplication with the projection data. This gain correction suppresses the influence of the basic contrast. Next, a second gain correction map is created in the image computer 14 from the projection data corrected in this manner. This method is repeated until the results differ from one another only by a value that is below a particular limit value.

Optionally, offset correction can additionally be performed.

The projection images corrected in this manner are then compiled in the control and evaluation system 11 using the image computer 12 to produce a tomosynthetic 3D overall image by means of reconstruction using filtered back-projection in a manner to which a person skilled in the art is familiar and are presented on a screen.

The first gain correction map used may also be the standard gain correction map provided by the manufacturer of the X-ray detector 7 or a pixel matrix that is continuously filled with the value "1" and corresponds to the detector matrix.

The control and evaluation system 11 is configured to perform the method described and has all the means required for this. Preferably, the control and evaluation system 11 comprises a data processing installation 15, designed to perform all the steps in accordance with the method described here that are connected to the processing of data. The data processing installation 15 preferably has a number of functional modules, each functional module being designed to perform a particular function or a number of particular functions in accordance with the method described. By way of example, the data processing installation 15 has an image computer 15 for ascertaining the correction map 22 and for correcting the projection data using this correction map 22. Suitable input and output devices are likewise provided, such as interfaces for inputting projection data and for outputting the corrected X-ray image.

Functional modules may be hardware modules or software modules. In other words, the invention, in so far as it relates to the data processing installation 15 and particularly the image computer 14, can be implemented either in the form of computer hardware or in the form of computer software or in a combination of hardware and software. In so far as the invention is implemented in the form of software, that is to say as a computer program, all of the functions described are implemented by computer program instructions when the computer program is executed in the data processing installation 15, particularly on a computer having a processor. In this case, the computer program instructions are implemented in a manner known per se in any programming language and can be provided for the computer in any form, for example in the form of data packets that are transmitted via a computer network or in the form of a computer program product that is stored on a floppy disk, a CD-ROM or another data storage medium.

Although the invention has been illustrated and described in more detail using the preferred exemplary embodiment, the invention is not restricted to the disclosed examples, and other variations can be derived therefrom by a person skilled in the art without departing from the scope of protection of the invention.

The following is a summary list of reference numerals and the corresponding structure used in the above description of the invention:

1 X-ray apparatus
2 X-ray source
3 X-ray radiation
4 examination object
5 compression plate
6 support plate
7 X-ray detector
8 single detector
9 reception area
11 control and evaluation system
12 control unit
13 data and supply lines
14 image computer
15 data processing installation
16 data and system bus lines
17 axis
18 normal
19 3D X-ray image
21 lowermost/bottommost layer
22 correction map

The invention claimed is:

1. An X-ray method, comprising:
recording digital projection data with a digital X-ray detector having a detector plane, the projection data being suitable for reconstruction of a tomosynthetic 3D X-ray image having layers;
creating a correction map for an electronic correction of the digital projection data recorded by the digital X-ray detector, the step of creating the correction map including a reconstruction of a lowermost layer of the 3D X-ray image from the digital projection data, the lowermost layer corresponding to the detector plane of the digital X-ray detector.

2. The method according to claim 1, which comprises reconstructing the lowermost layer by way of an unfiltered reconstruction method.

3. The method according to claim 1, wherein the 3D X-ray image is an image of an object to be examined.

4. The method according to claim 1, which comprises using an image representing the lowermost layer as a correction map or to create a correction map.

5. The method according to claim 4, which comprises using the image of the lowermost layer as a gain correction map or to create a gain correction map.

6. A method for electronic correction of digital projection data recorded by a digital X-ray detector, wherein the digital projection data are suitable for a reconstruction of a tomosynthetic 3D X-ray image, the method comprising: correcting the projection data with a correction map created by the method according to claim 1.

7. The method according to claim 6, which comprises correcting the projection data iteratively, wherein a creation of a respective further correction map includes a fresh reconstruction of the lowermost layer of the 3D X-ray image corresponding to the detector plane of the digital X-ray detector, of already corrected and reconstructed digital projection data.

8. An X-ray system, comprising:
a digital X-ray detector configured to acquire digital projection data suitable for reconstructing a tomosynthetic 3D X-ray image;
an apparatus for electronic correction of the digital projection data recorded with said digital X-ray detector, said apparatus being configured to correct the projection data using a correction map created on the basis of a method according to claim 1.

9. An apparatus for creating a correction map for electronic correction of digital projection data, the apparatus comprising:
an input for receiving digital projection data recorded by a digital X-ray detector, wherein the projection data are suitable for a reconstruction of a tomosynthetic 3D X-ray image; and
wherein the apparatus is configured to reconstruct a lowermost layer of the 3D X-ray image from the digital projection data, wherein the lowermost layer corresponds to a detector plane of the digital X-ray detector.

* * * * *